(12) United States Patent
Ho

(10) Patent No.: US 8,205,615 B1
(45) Date of Patent: Jun. 26, 2012

(54) SELF DIRECTING EXHAUST PORT ASSEMBLY

(75) Inventor: Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 1310 days.

(21) Appl. No.: 11/860,208

(22) Filed: Sep. 24, 2007

Related U.S. Application Data

(60) Provisional application No. 60/848,454, filed on Sep. 29, 2006.

(51) Int. Cl.
*A62B 9/02* (2006.01)
*A62B 18/02* (2006.01)
*A62B 18/10* (2006.01)
*A62B 7/00* (2006.01)
*A61M 16/00* (2006.01)

(52) U.S. Cl. ......... 128/205.24; 128/200.24; 128/207.12; 128/204.18; 128/206.21; 128/206.28

(58) Field of Classification Search .................. 128/857, 128/863, 200.24, 200.27, 200.28, 201.13, 128/202.27, 203.12, 203.25, 204.18, 204.21, 128/205.11, 205.25, 206.21, 206.27, 207.11, 128/207.13, 207.16, 205.24; 137/858, 527.8, 137/532–534; 251/247, 236, 231, 213, 336, 251/338

See application file for complete search history.

(56) References Cited

U.S. PATENT DOCUMENTS

| | | | | |
|---|---|---|---|---|
| 1,125,542 A | * | 1/1915 | Humphries | 128/207.18 |
| 1,287,149 A | * | 12/1918 | Water et al. | 128/206.24 |
| 2,254,854 A | * | 9/1941 | O'Connell | 128/206.28 |
| 3,905,390 A | * | 9/1975 | Pysh | 137/518 |
| 4,498,876 A | * | 2/1985 | Zemlicka | 440/89 R |
| 5,148,802 A | | 9/1992 | Sanders et al. | |
| 5,203,343 A | | 4/1993 | Axe et al. | |
| 5,301,667 A | * | 4/1994 | McGrail et al. | 128/205.14 |
| 5,313,937 A | | 5/1994 | Zdrojkowski et al. | |
| 5,425,358 A | * | 6/1995 | McGrail et al. | 128/205.24 |
| 5,433,193 A | | 7/1995 | Sanders et al. | |
| 5,438,981 A | * | 8/1995 | Starr et al. | 128/205.24 |
| 5,458,137 A | | 10/1995 | Axe et al. | |
| 5,535,738 A | | 7/1996 | Estes et al. | |
| RE35,339 E | | 10/1996 | Rappoport | |
| 5,632,269 A | | 5/1997 | Zdrojkowski et al. | |
| 5,647,355 A | * | 7/1997 | Starr et al. | 128/205.24 |
| 5,794,615 A | | 8/1998 | Estes | |
| 5,803,065 A | | 9/1998 | Zdrojkowski et al. | |
| 5,937,851 A | | 8/1999 | Serowski et al. | |
| 6,029,664 A | | 2/2000 | Zdrojkowski et al. | |
| 6,083,141 A | * | 7/2000 | Hougen | 482/13 |
| 6,085,747 A | | 7/2000 | Axe et al. | |
| 6,105,575 A | | 8/2000 | Estes et al. | |
| 6,112,745 A | | 9/2000 | Lang | |

(Continued)

FOREIGN PATENT DOCUMENTS

| | | |
|---|---|---|
| WO | WO 98/34665 | 8/1998 |
| WO | WO 00/78381 | 12/2000 |

*Primary Examiner* — Annette Dixon
(74) *Attorney, Agent, or Firm* — Michael W. Haas

(57) ABSTRACT

An exhaust port assembly adapted for delivering a breathing gas to a patient. The exhaust port assembly includes a body and a mechanism associated with the body. The mechanism, in response to a motive force, is structured to control the direction of a flow of exhaust gas discharged through at least some of a number of exhaust ports. A system and method are also provided.

4 Claims, 11 Drawing Sheets

U.S. PATENT DOCUMENTS

| | | | |
|---|---|---|---|
| 6,581,594 B1 * | 6/2003 | Drew et al. | 128/204.18 |
| 6,615,830 B1 * | 9/2003 | Serowski et al. | 128/202.27 |
| 6,851,425 B2 * | 2/2005 | Jaffre et al. | 128/204.18 |
| 7,559,327 B2 * | 7/2009 | Hernandez | 128/207.18 |

* cited by examiner

SELF DIRECTING EXHAUST PORT ASSEMBLY

CROSS-REFERENCE TO RELATED APPLICATIONS

This application claims priority under 35 U.S.C. §119(e) from provisional U.S. patent application No. 60/848,454 filed Sep. 29, 2006 the contents of which are incorporated herein by reference.

BACKGROUND OF THE INVENTION

1. Field of the Invention

The present invention pertains to an exhaust port assembly for use in a pressure support system and, in particular, to a self-directing exhaust port assembly with enhanced noise reduction and gas diffusion capabilities. The present invention also pertains to a pressure support system which employs such a self-directing exhaust port assembly and a method of providing a regimen of respiratory therapy to a patient.

2. Description of the Related Art

It is well known to treat a patient with a non-invasive positive pressure support therapy, in which a flow of breathing gas is delivered to the airway of a patient at a pressure greater than the ambient atmospheric pressure. For example, it is known to use a continuous positive airway pressure (CPAP) device to supply a constant positive pressure to the airway of a patient throughout the patient's respiratory cycle to treat obstructive sleep apnea (OSA), as well as other cardio-pulmonary disorders, such at congestive heart failure (CHF) and cheynes-stokes respiration (CSR). Examples of such CPAP devices include the REMstar® family of CPAP devices manufactured by Respironics, Inc. of Murrysville, Pa.

A "bi-level" non-invasive positive pressure therapy, in which the pressure of gas delivered to the patient varies with the patient's breathing cycle, is also known. For example, a "bi-level" pressure support system provides an inspiratory positive airway pressure (IPAP) that is greater than an expiratory positive airway pressure (EPAP). IPAP refers to the pressure of the flow of gas delivered to the patient's airway during the inspiratory phase; whereas EPAP refers to the pressure of the flow of gas delivered to the patient's airway during the expiratory phase. Such a bi-level mode of pressure support is provided by the BiPAP® family of devices manufactured and distributed by Respironics, Inc. and is taught, for example, in U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., the contents of each of which are incorporated herein by reference.

Auto-titration positive pressure therapy is also known. With auto-titration positive pressure therapy, the pressure of the flow of breathing gas provided to the patient changes based on the detected conditions of the patient, such as whether the patient is snoring or experiencing an apnea, hypopnea, or upper airway resistance. An example of a device that adjusts the pressure delivered to the patient based on whether or not the patient is snoring is the Virtuoso® CPAP family of devices manufactured and distributed by Respironics, Inc. This auto-titration pressure support mode is taught, for example, in U.S. Pat. Nos. 5,203,343; 5,458,137 and 6,087,747 all to Axe et al., the contents of which are incorporated herein by reference.

A further example of an auto-titration pressure support device that actively tests the patient's airway to determine whether obstruction, complete or partial, could occur and adjusts the pressure output to avoid this result is the Tranquility® Auto CPAP device, also manufactured by Respironics, Inc. This auto-titration pressure support mode is taught in U.S. Pat. No. 5,645,053 to Remmers et al., the content of which is also incorporated herein by reference.

Other modes of providing positive pressure support to a patient are known. For example, a proportional assist ventilation (PAV®) mode of pressure support provides a positive pressure therapy in which the pressure of gas delivered to the patient varies with the patient's breathing effort to increase the comfort to the patient. U.S. Pat. Nos. 5,044,362 and 5,107,830 both to Younes, the contents of which are incorporated herein by reference, teach a pressure support device capable of operating in a PAV® mode. Proportional positive airway pressure (PPAP) devices deliver breathing gas to the patient based on the flow generated by the patient. U.S. Pat. Nos. 5,535,738; 5,794,615; and 6,105,573 all to Estes et al., the contents of each of which are incorporated herein by reference, teach a pressure support device capable of operating in a PPAP mode.

For purposes of the present invention, the phases "pressure support device", "pressure generating device", and/or "pressure generator" (used interchangeable herein) refer to any medical device adapted for delivering a flow of breathing gas to the airway of a patient, including a ventilator, CPAP, PAV®, PPAP, or bi-level pressure support device. The phrases "pressure support system" and/or "positive pressure support system" (used interchangeable herein) include any arrangement or method employing a pressure support device and adapted for delivering a flow of breathing gas to the airway of a patient.

In a conventional pressure support system, a flexible conduit couples the pressure support device to a patient interface device. The flexible conduit forms part of what is typically referred to as a "patient circuit" which carries the flow of breathing gas from the pressure support device to patient interface device. The patient interface device connects the patient circuit with the airway of the patient so that the flow of breathing gas is delivered to the patient's airway. Examples of patient interface devices include a nasal mask, nasal and oral mask, full face mask, nasal cannula, oral mouthpiece, tracheal tube, endotracheal tube, or hood.

In a non-invasive pressure support system, i.e., a system that remains outside the patient, a single-limb patient circuit is typically used to communicate the flow of breathing gas to the airway of the patient. An exhaust port (also referred to as an exhalation vent, exhalation port, and/or exhaust vent) is provided in the patient circuit and/or the patient interface device to allow exhaust gas, such as the exhaled gas from the patient, to vent to atmosphere.

A variety of exhalation ports are known for venting gas from a single-limb patient circuit. For example, U.S. Pat. No. Re. 35,339 to Rappoport discloses a CPAP pressure support system wherein a few exhaust ports are provided directly on the patient interface device, i.e., in the wall of the mask. However, this exhaust port configuration results in a relatively direct stream of exhaust gas being directed from the mask or patient circuit. Direct streaming of the flow of exhaust gas is undesirable, because a typical CPAP system is intended to be used while the patient is asleep. Sleep for the patient or the patient's bed partner is disturbed if a stream of gas is directed at the patient or at the patient's bed partner.

The exhaust port assembly described in published PCT Application No. WO 98/34665 to Kwok is directed to minimizing the noise associated with the leakage of exhaust gas. This is allegedly accomplished by providing an elastomeric ring around the perimeter of the exhaust port. This exhaust port configuration, however, does not solve the problem of preventing a generally direct or concentrated stream of gas from being directed from the mask onto the patient or the patient's sleep partner.

U.S. Pat. No. 5,937,851 to Serowski et al., U.S. Pat. No. 6,112,745 to Lang, and published PCT Application No. WO 00/78381 to Gunaratnam et al. all disclose exhalation ports for a positive pressure support system. Each of the exhalation ports taught by these references attempts to solve the problem of preventing a stream of gas from being directed onto the patient or onto the patient's bed partner by controlling the direction of the flow of exhaust gas. For example, each of these references teaches directing the flow of exhaust gas back along the patient circuit rather than directly outward away from the patient. However, the relative direction of the stream of gas flow changes each time the patient assumes a new sleeping position, and depending on the positioning of the patient circuit, the stream of concentrated gas may be directed onto the patient or the patient's sleep partner.

Accordingly, a need exists for an apparatus and method for providing an improved exhaust port which is adapted to direct the discharge direction of a flow of exhaust gas away from the patient and/or the patient's sleep partner regardless of the patient's position, and which overcomes these and other problems associated with known systems.

SUMMARY OF THE INVENTION

In accordance with an aspect of the present invention a self-directing exhaust port assembly comprises a mechanism structured to control the direction of a flow of exhaust gas discharged through at least some of a number of exhaust ports, wherein the mechanism is responsive to a motive force.

According to another aspect of the present invention, an exhaust port assembly comprises a body and a mechanism associated with the body, wherein the mechanism, in response to a motive force, is structured to control the direction of a flow of exhaust gas discharged through at least some of a number of exhaust ports.

According to another aspect of the present invention, a method for providing a regimen of respiratory therapy to a patient comprises communicating a flow of breathing gas to an airway of such a patient via a system with an exhaust port assembly having a self-directing mechanism and a number of exhaust ports, selecting automatically, in response to a change in the orientation of the exhaust port assembly, a direction to discharge a flow of exhaust gas through at least some of the number of exhaust ports, and discharging the flow of exhaust gas through the ports in the direction selected.

According to another aspect of the present invention, a system adapted to provide a regimen of respiratory therapy to a patient comprises a gas flow generator structured to produce a flow of breathing gas, a patient interface device structured to communicate the flow of breathing gas to an airway of such a patient, an exhaust port assembly, and a patient circuit structured to couple the gas flow generator to the patient interface device. The exhaust port assembly comprises a mechanism structured to control the direction of a flow of exhaust gas discharged through at least some of a number of exhaust ports, wherein the mechanism is responsive to a motive force.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 3A-5A are detailed end views of the positioning of the exhaust port assembly of FIGS. 3-5, respectively.

DETAILED DESCRIPTION OF THE EXEMPLARY EMBODIMENTS

Figure 1:
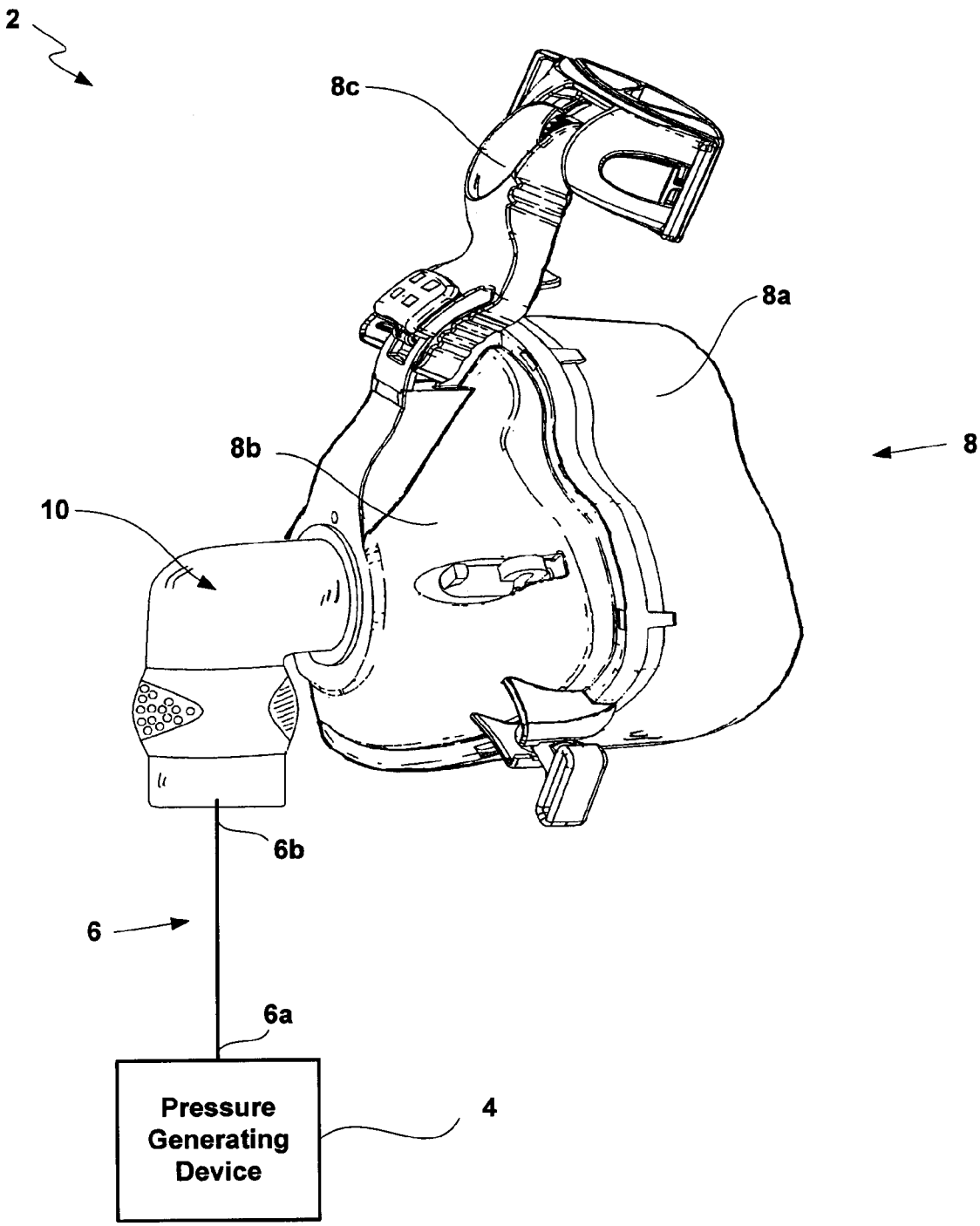
FIG. 1 is a schematic diagram of a pressure support system adapted to provide a regimen of respiratory therapy to a patient according to one embodiment of the present invention.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

A system 2 adapted to provide a regimen of respiratory therapy to a patient according to one embodiment is generally shown in FIG. 1. System 2 includes a pressure generating device 4, a patient circuit 6, a patient interface device 8, and an exhaust port assembly 10. Although system 2 is discussed as including a pressure generating device 4, a patient circuit 6, a patient interface device 8, and an exhaust port assembly 10, it is contemplated that other systems may be employed while remaining within the scope of the present invention. For example, and without limitation, a system in which the pressure generating device is coupled to a patient interface device having an integrated exhaust port assembly is contemplated.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Respironics, Inc. of Murrysville, Pa.), and auto-titration pressure support devices.

Patient circuit 6 is structured to communicate the flow of breathing gas from pressure generating device 4 to patient interface device 8. Typically, patient circuit 6 includes a conduit or tube, a first end 6a of which couples with pressure generating device 4 and a second end 6b of which couples with patient interface device 8. In the current embodiment, second end 6b is coupled with exhaust port assembly 10 which, in turn, is coupled with patient interface device 8. As will be discussed below, however, other arrangements within the scope of the present invention are contemplated.

Patient interface 8 is typically a nasal or nasal/oral mask structured to be placed on and/or over the face of a patient. Any type of patient interface device 8, however, which facilitates the delivery of the flow of breathing gas to, and the removal of a flow of exhalation gas from, the airway of such a patient may be used while remaining within the scope of the present invention. In the embodiment shown in FIG. 1, patient interface 8 includes a cushion 8a, a rigid shell 8b, and a forehead support 8c. Straps (not shown) may be attached to shell 8b and forehead support 8c to secure patient interface 8 to the patient's head.

An opening in shell 8b, to which exhaust port assembly 10 is coupled, allows the flow of breathing gas from pressure generator device 4 to be communicated to an interior space defined by shell 8b and cushion 8a, and then, to the airway of a patient. The opening in shell 8b also allows the flow of exhalation gas (from the airway of such a patient) to be communicated to the exhaust port assembly 10 in the current embodiment. Although illustrated as a separate component in FIG. 1, it is contemplated that exhaust port assembly 10 may be incorporated into, for example and without limitation, patient interface 8 and/or patient circuit 6 while remaining within the scope of the present invention.

Figure 2:
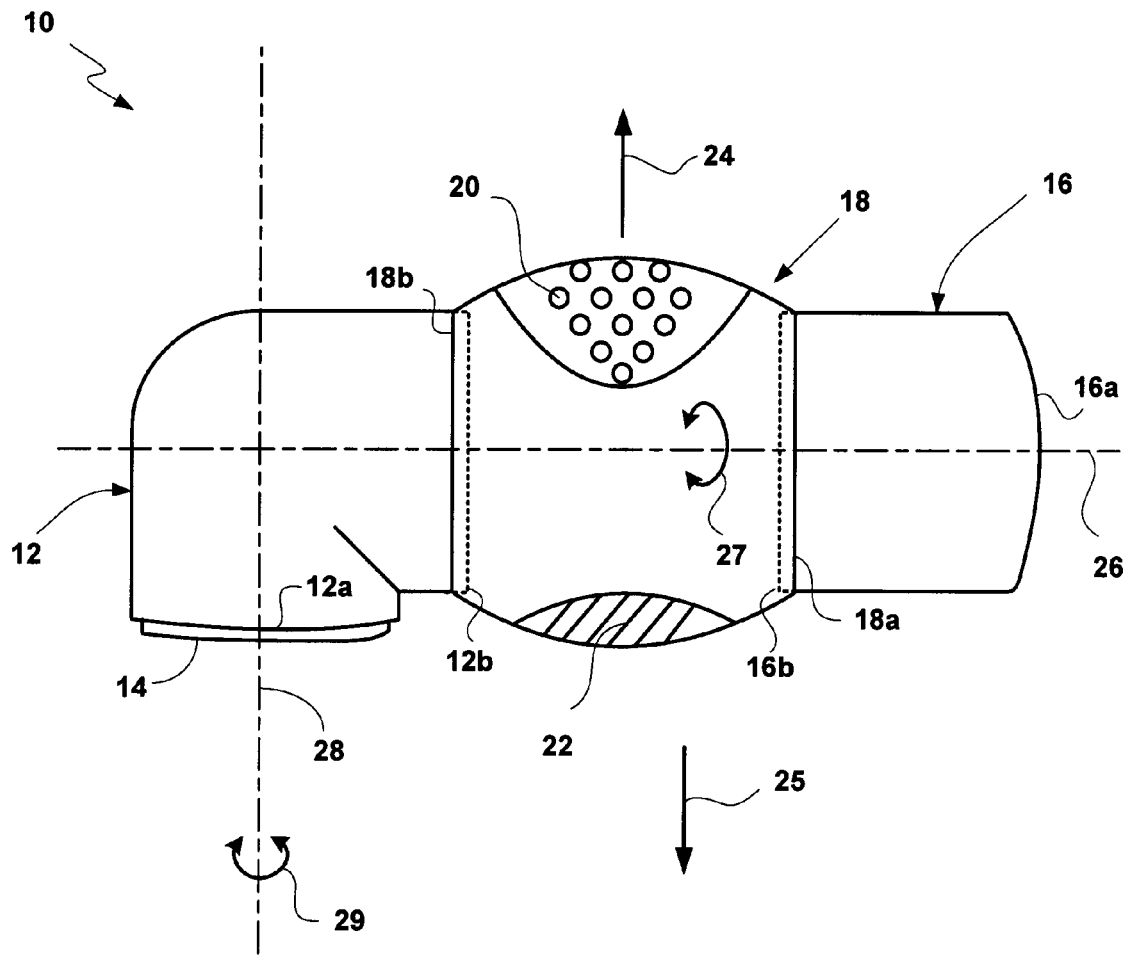
FIG. 2 is a side view of an exhaust port assembly according to one embodiment of the present invention.

Referring now to FIG. 2, a side view of exhaust port assembly 10 of FIG. 1 is illustrated. Exhaust port assembly 10 includes a two-piece body connected by a self-directing mechanism for controlling the direction of a flow of gas. More specifically, exhaust port assembly 10 has an inlet member 16 and an outlet member 12 connected by a self-directing mechanism 18 (such as, without limitation, sleeve 18). Inlet member 16 is structured to receive a flow of breathing gas from pressure generating device 4 (FIG. 1). In the current embodiment, inlet member 16 has a first end 16a structured to couple with the second end 6b of conduit 6 (wherein the first end 6a of conduit 6 is coupled with pressure generating device 4). Outlet member 12 has a first end 12a structured to couple with patient interface 8, which as discussed above, is adapted to deliver the flow of breathing gas to, and remove a flow of exhalation gas from, the airway of a patient. In the current embodiment, outlet member 12 is shaped as an elbow and first end 12a includes a flange 14 structured to rotatably couple exhaust port assembly 10 with rigid shell 8b. As a result, exhaust port assembly 10 can rotate relative to rigid shell 8b (as indicated by arrow 29) about an axis 28.

Although outlet member 12 is illustrated as an elbow and inlet member 16 is illustrated as a substantially linear piece, other shapes may be employed while remaining within the scope of the present invention. For example, an exhaust port assembly with both a linear outlet member 12 and a linear inlet member 16 is contemplated. Such an exhaust port assembly may be employed, for instance, with a patient interface device having an integrated discharge elbow.

Mechanism 18 is structured to couple with both inlet member 16 and outlet member 12. In the current embodiment, a first end 18a of mechanism 18 rotatably couples with a second end 16b of inlet member 16 and a second end 18b of mechanism 18 rotatably couples with a second end 12b of outlet member 12.

Mechanism 18 includes a counter weight 22 and a number of ports 20. Counter weight 22 is generally a metal alloy insert (e.g., copper; brass; iridium; stainless steel; etc.); however, any dense material with a high molecular weight may be used while remaining within the scope of the present invention. It also contemplated that other arrangements may be employed, for example, a portion of mechanism 18 may be provided with additional wall thickness such that counter weight 22 is of unitary construction with mechanism 18. In the current embodiment, mechanism 18 is structured such that a gravitational force acts upon counter weight 22 causing mechanism 18 to rotate about axis 26. Although gravity is employed as the motive force in this embodiment, it is contemplated that other motive forces (such as and without limitation, magnetic force, electro-magnetic force, etc.) may be employed instead of, or in combination with, gravitational force. For instance, a bar magnet may be used as counter weight 22 and another magnet (placed, for example, under the patient's pillow, on the patient's mattress, on the mask, on the patient circuit, etc.) may cause a magnetic force to act upon counter weight 22 in addition to gravitational force. Arrangements in which attractive magnetic forces and/or repulsive magnetic forces are employed are contemplated.

Ports 20 are structured to discharge a flow of exhaust gas (indicated by arrow 24) to atmosphere. The flow of exhaust gas 24 may include, for example and without limitation, the flow of breathing gas, the flow of exhalation gas, and/or a mixture of the two. Ports 20 may be arranged and/or adapted to reduce the amount of noise produced by discharging the flow of exhaust gas 24 through ports 20. For example, ports 20 may be arranged in a specific pattern, have a specific shape/design (e.g., slotted, circular, oval, tapered, etc.), and/or employ inserts (e.g., elastomeric rings) around the perimeter of the exhaust ports 20.

In the current embodiment, ports 20 are located substantially 180 degrees away from counter weight 22. Accordingly, a motive force (here, gravitational force indicated by arrow 25) causes mechanism 18 to rotate such that counter weight 22 is located substantially at the bottom of mechanism 18 (i.e., towards gravitational force 25) and ports 20 are located substantially at the top of mechanism 18. As a result, flow of exhaust gas 24 is discharged substantially upward. Counter weight 22 and ports 20 may be arranged other than 180 degrees apart (thus changing the general direction that the flow of exhaust gas 24 is discharged) while remaining within the scope of the present invention.

Mechanism 18 is adapted to freely rotate relative to inlet member 16 and/or outlet member 12 about an axis 26 (as indicated by arrow 27). As a result, mechanism 18 remains substantially stationary when the exhaust port assembly 10 undergoes a change in the orientation. For example when inlet member 16 and/or outlet member 12 rotate relative to axis 26, gravitational force 25 acting on counter weight 22 causes mechanism 18 to remain substantially stationary such that ports 20 continue to point up. As a result, flow of exhaust gas 24 is discharged through ports 20 in a substantially constant direction (i.e., independent of movement of the inlet member 16 and/or outlet member 12 relative to axis 26).

Figure 3:
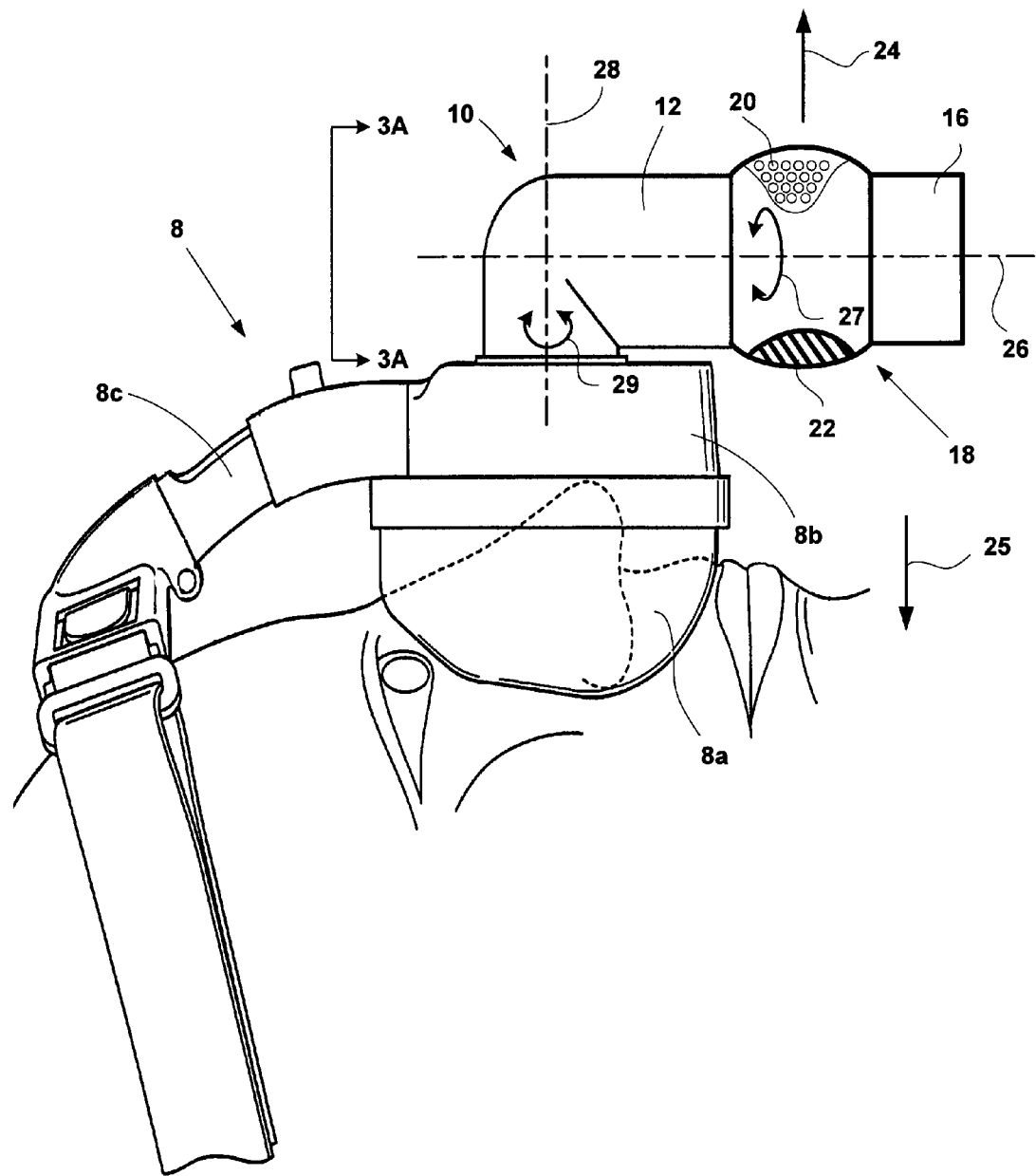
FIGS. 3-5 illustrate a patient interface device incorporating the exhaust port assembly of FIG. 2 as being worn by a patient in different sleeping positions.
Figure 4A:
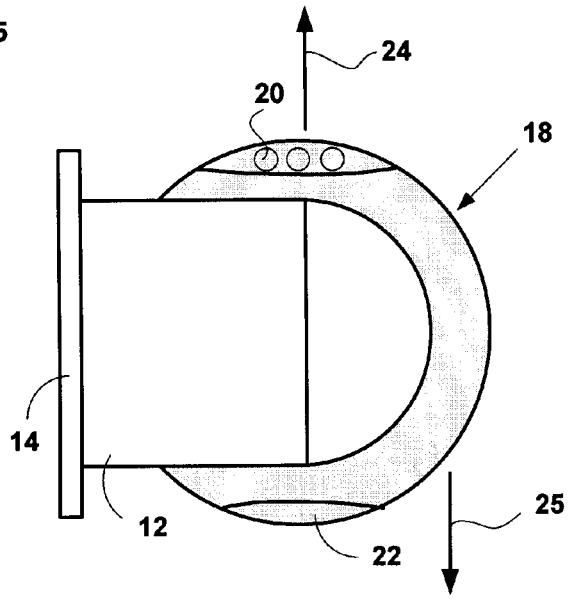
Figure 5A:
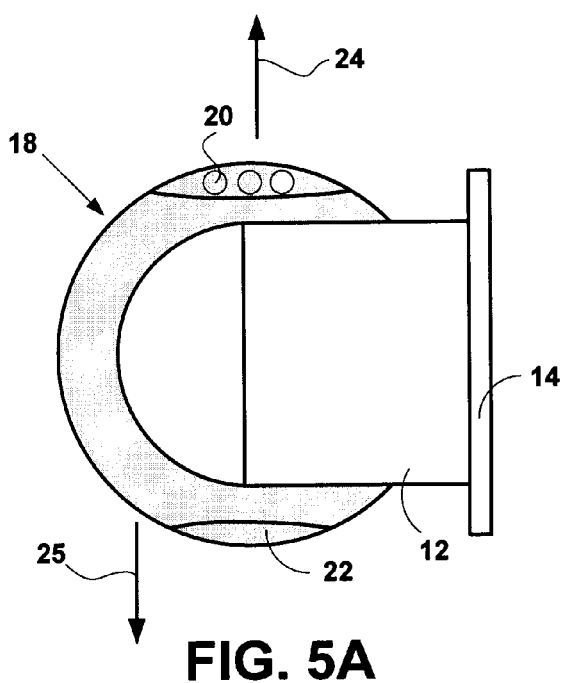
Figure 4:
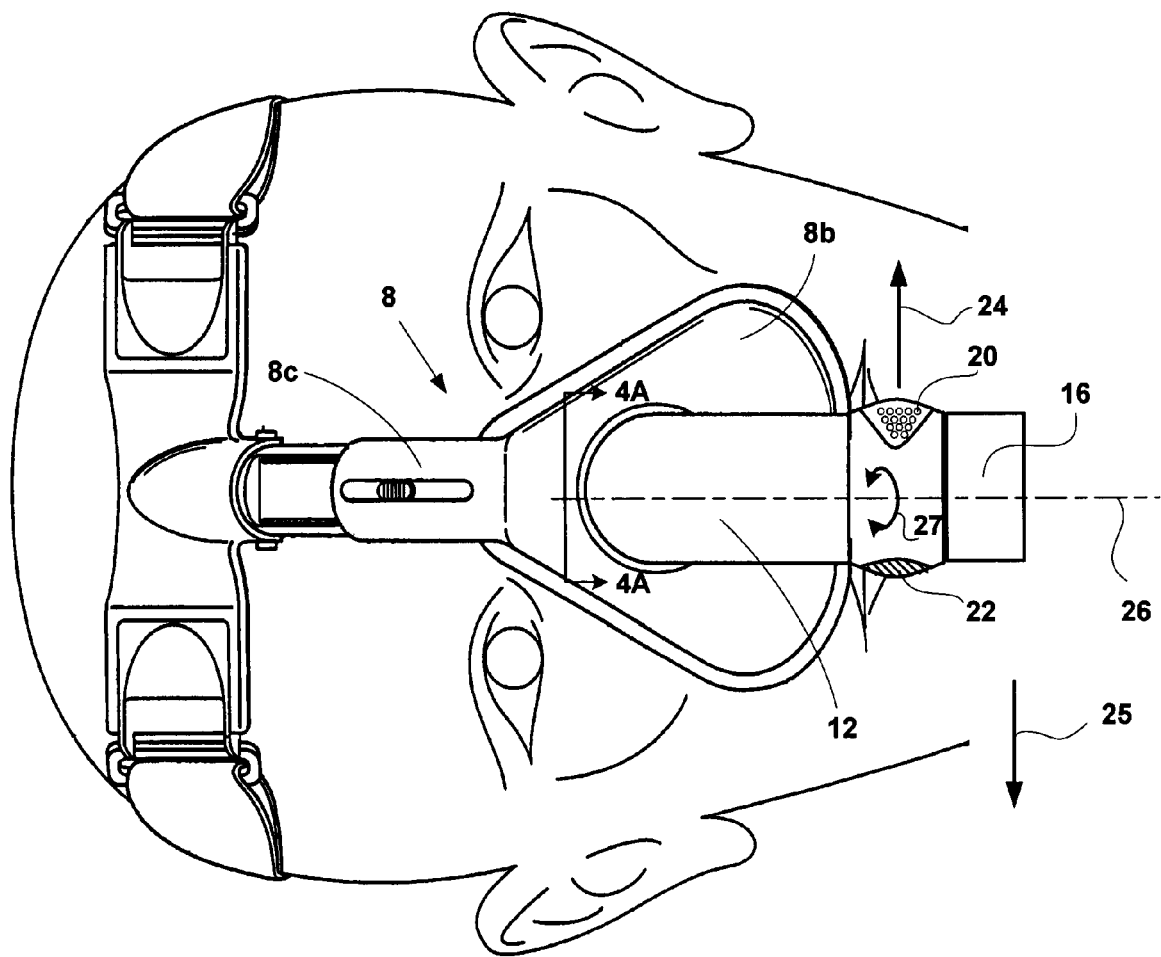
Figure 5:
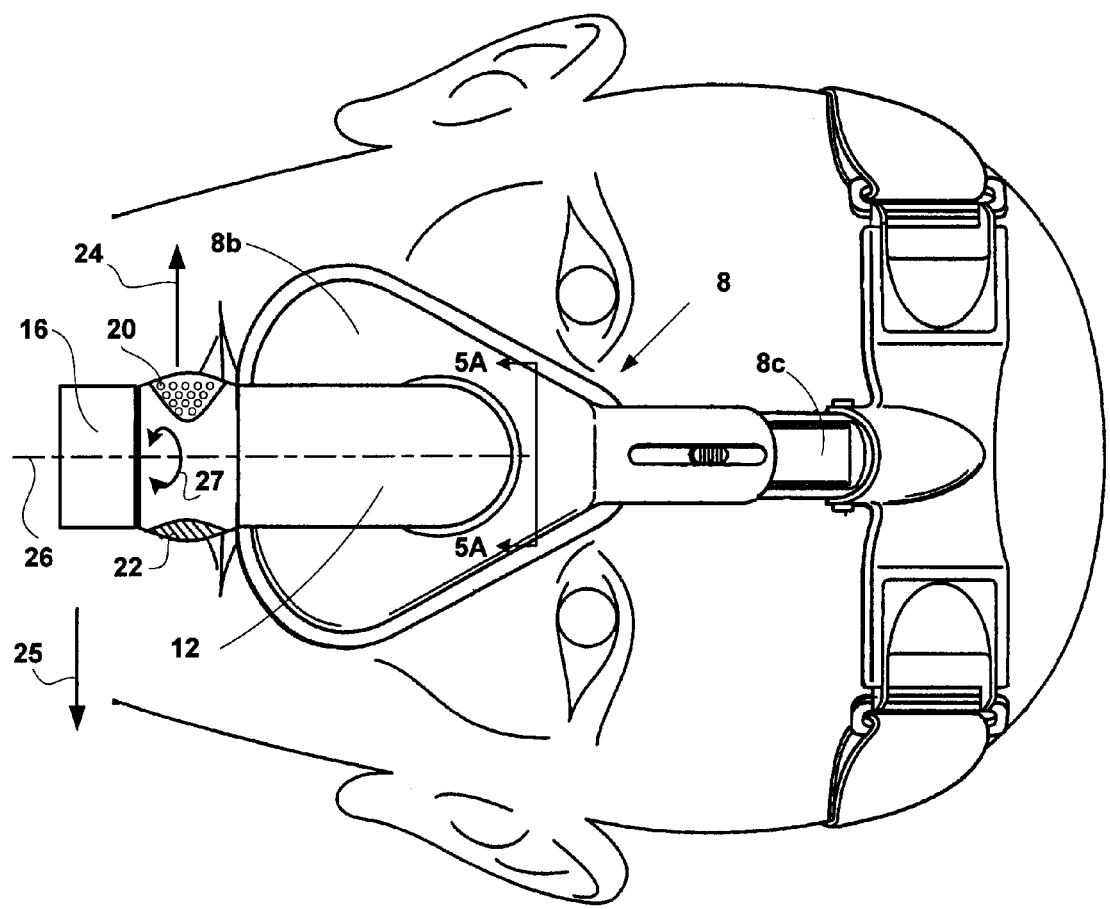

Referring now to FIGS. 3-5, a patient interface device 8 and exhaust port assembly 10 are illustrated as being worn by a patient. In FIG. 3, the patient is shown resting on his back.

Figure 3A:
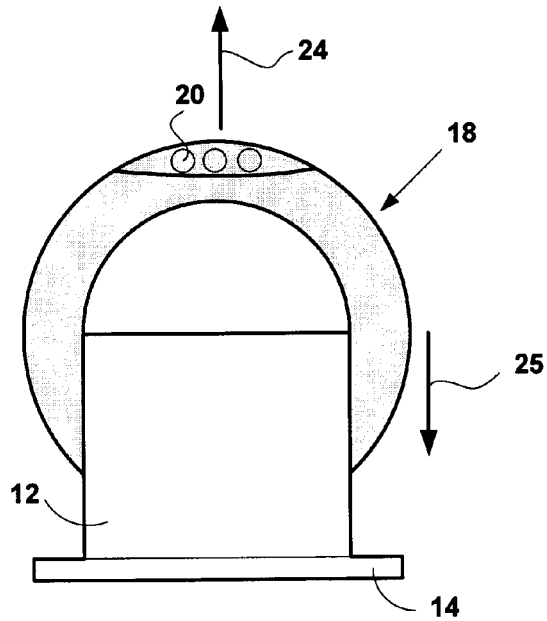

Gravitational pull 25 on counter weight 22 causes mechanism 18 to rotate about axis 26 (as indicated by arrow 27) such that ports 20 point upward. As a result, flow of exhaust gas 24, discharged through ports 20, is directed away from the patient and away from the patient's bed mate. It should be noted that ports 20 continue to point upward when exhaust port assembly 10 is rotated about axis 28 (as indicated by arrow 29). FIG. 3A illustrates an end view of exhaust port assembly 10 when the patient is resting on his back.

In FIG. 4, the patient is shown resting on his right side. Gravitational pull 25 on counter weight 22 causes mechanism 18 to rotate about axis 26 (as indicated by arrow 27) such that ports 20 continue to point upward. As seen in the end view of exhaust port assembly 10 in FIG. 4A, mechanism 18 rotates independently of the movement of inlet member 16 and/or outlet member 12. Comparing FIGS. 3 and 3A to FIGS. 4 and 4A, outlet member 12 is rotated approximately −90 degrees when the patient moves from resting on his back to resting on his right side. Mechanism 18, however, remains in substantially the same position relative to axis 26. Accordingly, flow of exhaust gas 24, discharged through ports 20, remains directed away from the patient and away from the patient's bed mate.

In FIG. 5, the patient is shown resting on his left side. Gravitational pull 25 on counter weight 22 causes mechanism 18 to rotate about axis 26 (as indicated by arrow 27) such that ports 20 continue to point upward. As seen in the end view of exhaust port assembly 10 in FIG. 5A, mechanism 18 rotates independently of the movement of inlet member 16 and/or outlet member 12. Comparing FIGS. 3 and 3A to FIGS. 5 and 5A, outlet member 12 is rotated approximately 90 degrees when the patient moves from resting on his back to resting on his left side. Mechanism 18, however, remains in substantially the same position relative to axis 26. Accordingly, flow of exhaust gas 24, discharged through ports 20, remains directed away from the patient and away from the patient's bed mate.

Figure 6:
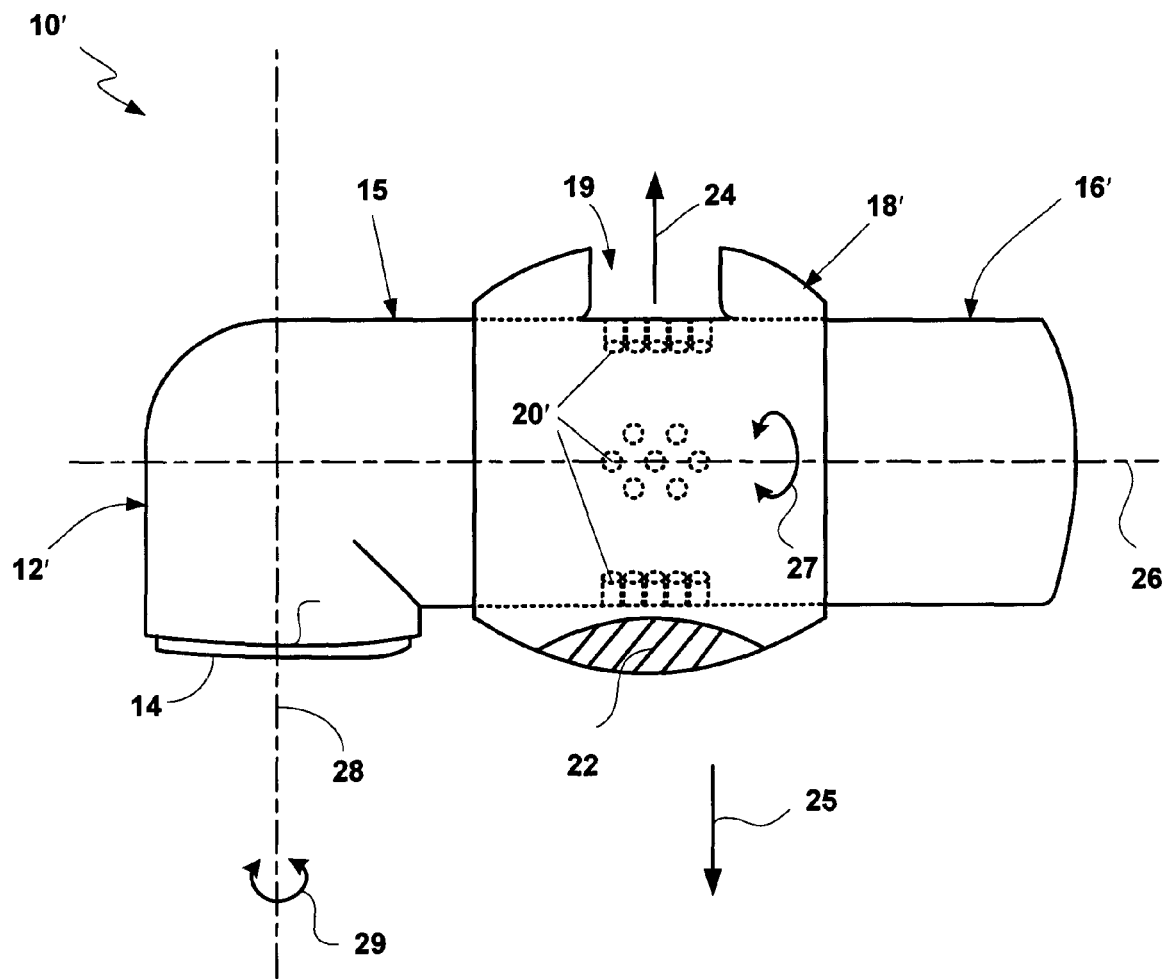
FIG. 6 illustrates an exhaust port assembly according to another embodiment of the present invention.

An exhaust port assembly 10' according to an alternative embodiment is shown in FIG. 6. Exhaust port assembly 10' includes a self-directing mechanism 18' and a one-piece body 15 with an inlet 16' and an outlet 12'. Body 15 has a number of ports 20' located in wall thereof. Mechanism 18' is adapted to freely rotate relative to body 15 about axis 26 (as indicated by arrow 27). Mechanism 18' has a counter weight 22 and an opening 19. Responsive to a motive force (here, gravitational force 25), mechanism 18' rotates such that opening 19 aligns with some of the number of ports 20'. Accordingly, flow of exhaust gas 24, discharged through ports 20', is exhausted in a substantially constant direction independent of movement of body 19 and directed away from the patient and the patient's bed mate.

Figure 7:
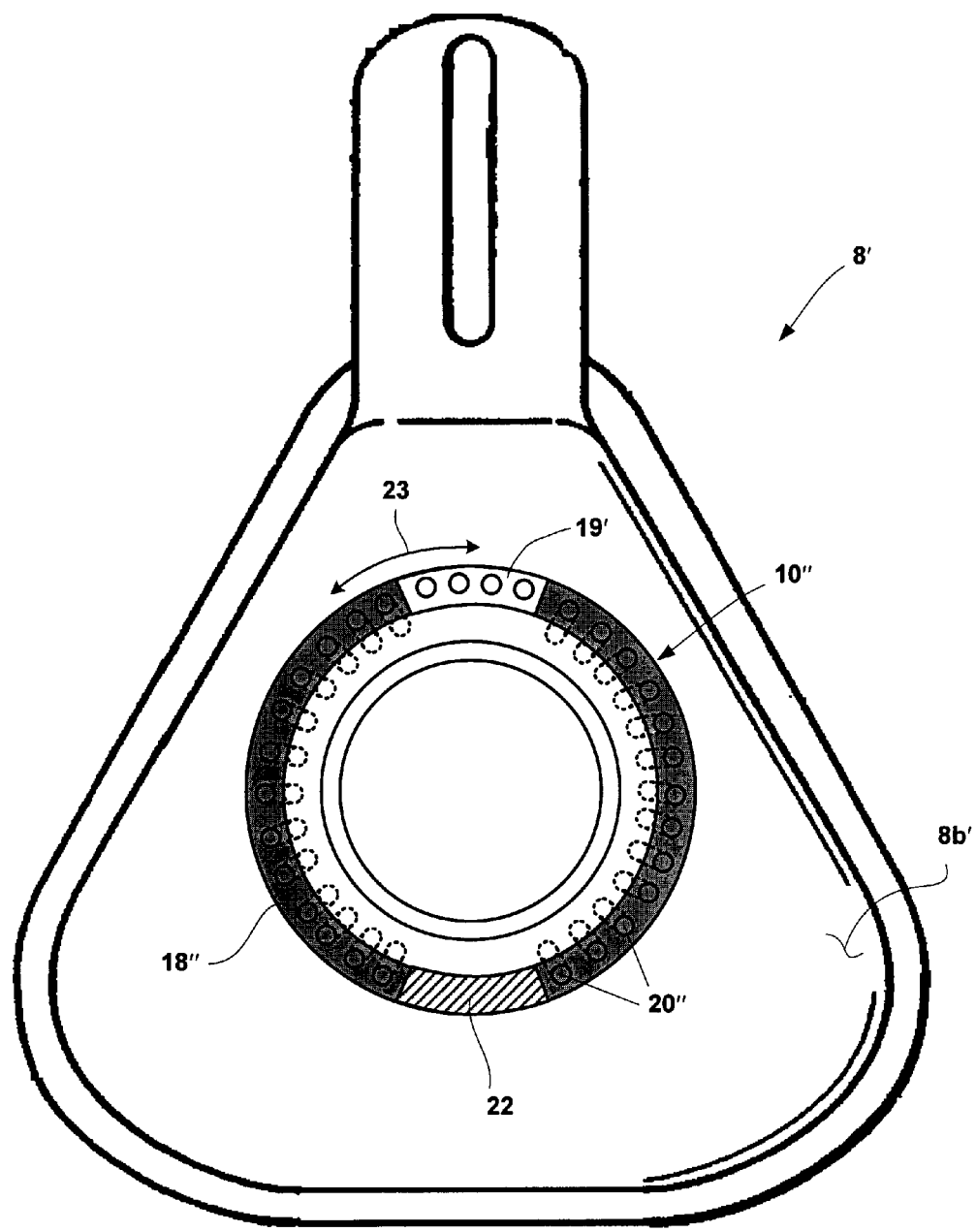
FIG. 7 illustrates a patient interface device and an exhaust port assembly according to another embodiment of the present invention.

FIG. 7 illustrates an exhaust port assembly 10" that is integrated directly into rigid shell 8b' of patient interface device 8' according to one embodiment. A number of exhaust ports 20", arranged in a generally circular pattern, extend through rigid shell 8b'. A self-directing mechanism 18" (e.g., a ring 18") having an opening 19' and a counter weight 22 controls the direction of a flow of exhaust gas (not shown) discharged from exhaust ports 20". When the orientation of the exhaust port assembly is changed (e.g., when a patient changes resting positions from resting on his back to resting on his right side), a motive force (here, gravitational force 25) acting upon counter weight 22 causes ring 18" to rotate (as indicated by arrow 23) such that opening 19' aligns with certain ports 20". In the current embodiment, at least some of exhaust ports 20" are angled such that the direction of the flow of exhaust gas exiting therefrom may be further controlled. When a patient is resting on his right side, for example, exhaust ports 20" are angled such that the flow of exhaust gas is directed substantially upward.

Figure 8:
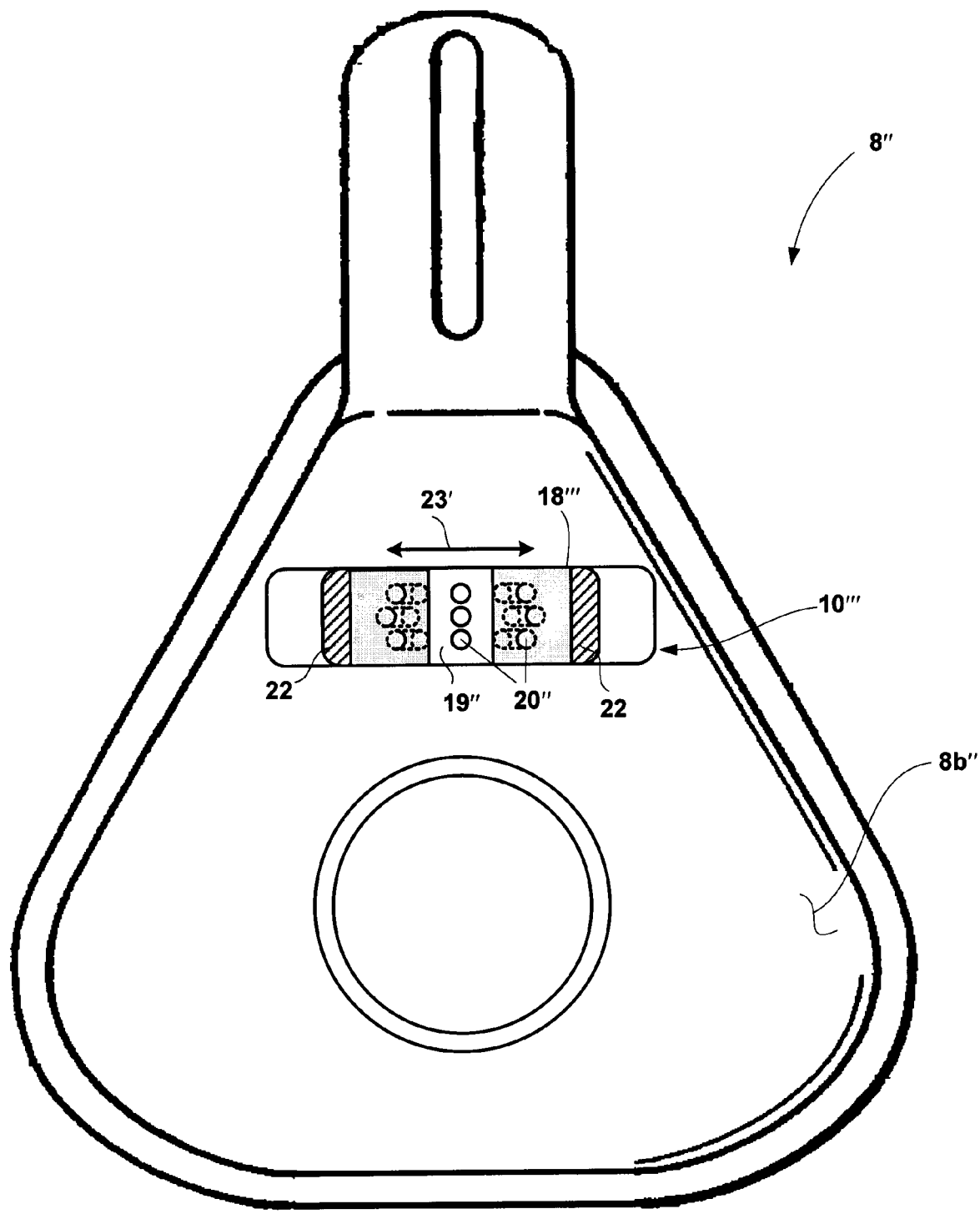
FIGS. 8-9 illustrate a patient interface device and an exhaust port assembly according to another embodiment of the present invention.
Figure 9:
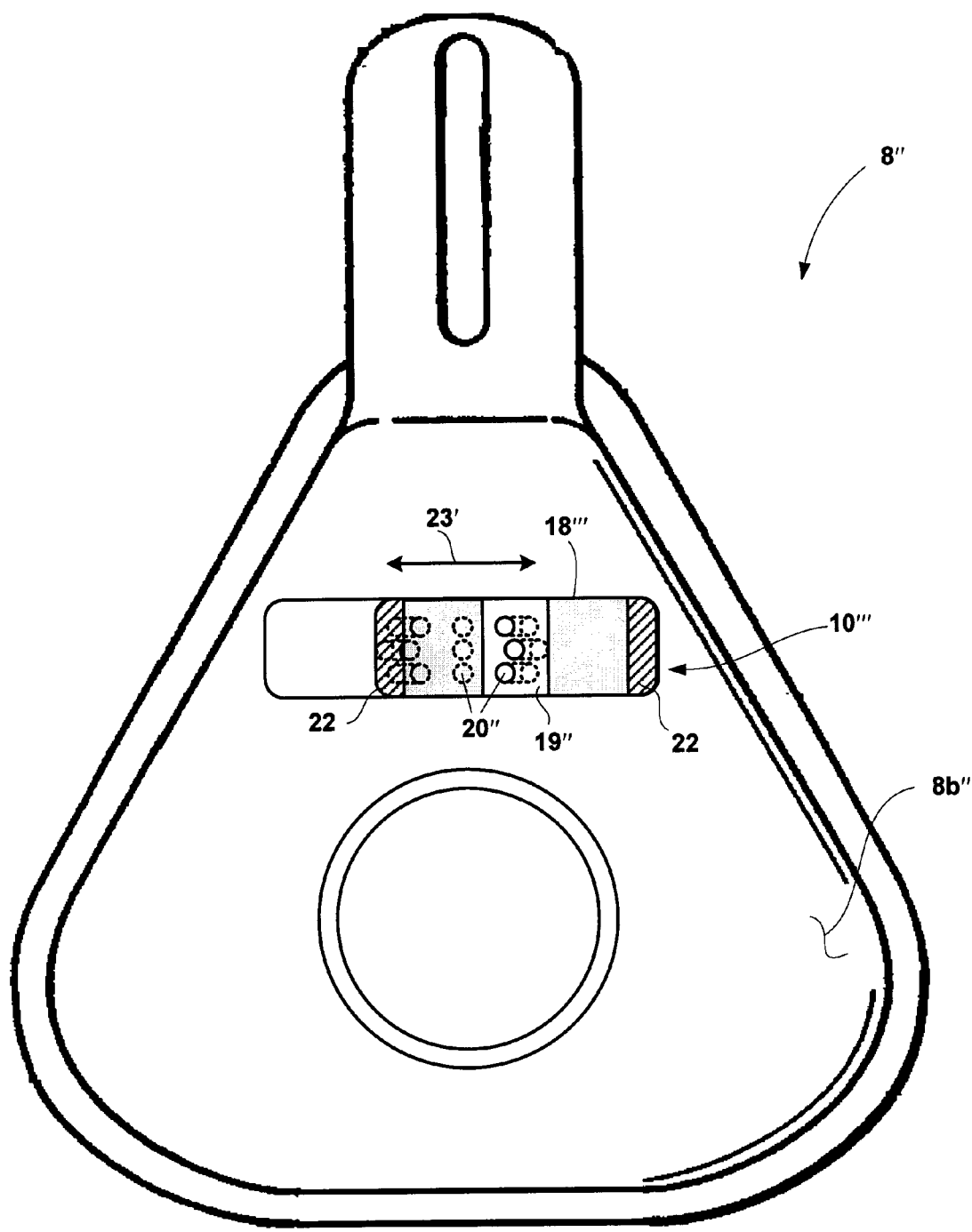

FIGS. 8 and 9 illustrate an exhaust port assembly 10''' that is integrated directly into rigid shell 8b" of patient interface device 8" according to an alternative embodiment in which three sets of exhaust ports 20''' extend through rigid shell 8b". Generally, the first set of exhaust ports 20" are perpendicular relative to the rigid shell 8b", the second set of exhaust ports 20" are at a first angle relative to the rigid shell 8b", and the second set of exhaust ports are at a second angle relative to the rigid shell 8b".

A self-directing mechanism 18''' (e.g., a slide 18''') having an opening 19" and counter weights 22 controls the direction of a flow of exhaust gas (not shown) discharged from exhaust ports 20". In the current embodiment, slide 18''' is structured to move laterally (as indicated by arrow 23') within a channel in rigid shell 8b". Where a patient is resting on his back, mechanism 18''' is adapted such that opening 19" is aligned with the first set of exhaust ports 20" (as shown in FIG. 8) and the flow of exhaust gas is directed up, away from the patient. When the orientation of the exhaust port assembly changes, for example, when a patient changes resting positions from resting on his back to resting on his left side, a motive force (here, gravitational force) on counter weights 22 causes slide 18''' to move such that opening 19" aligns with the second set of exhaust ports 20" (see FIG. 9). As discussed above, the second set of ports are angled relative to rigid shell 8b" so that the flow of exhaust gas is discharged substantially upward.

Figure 10:
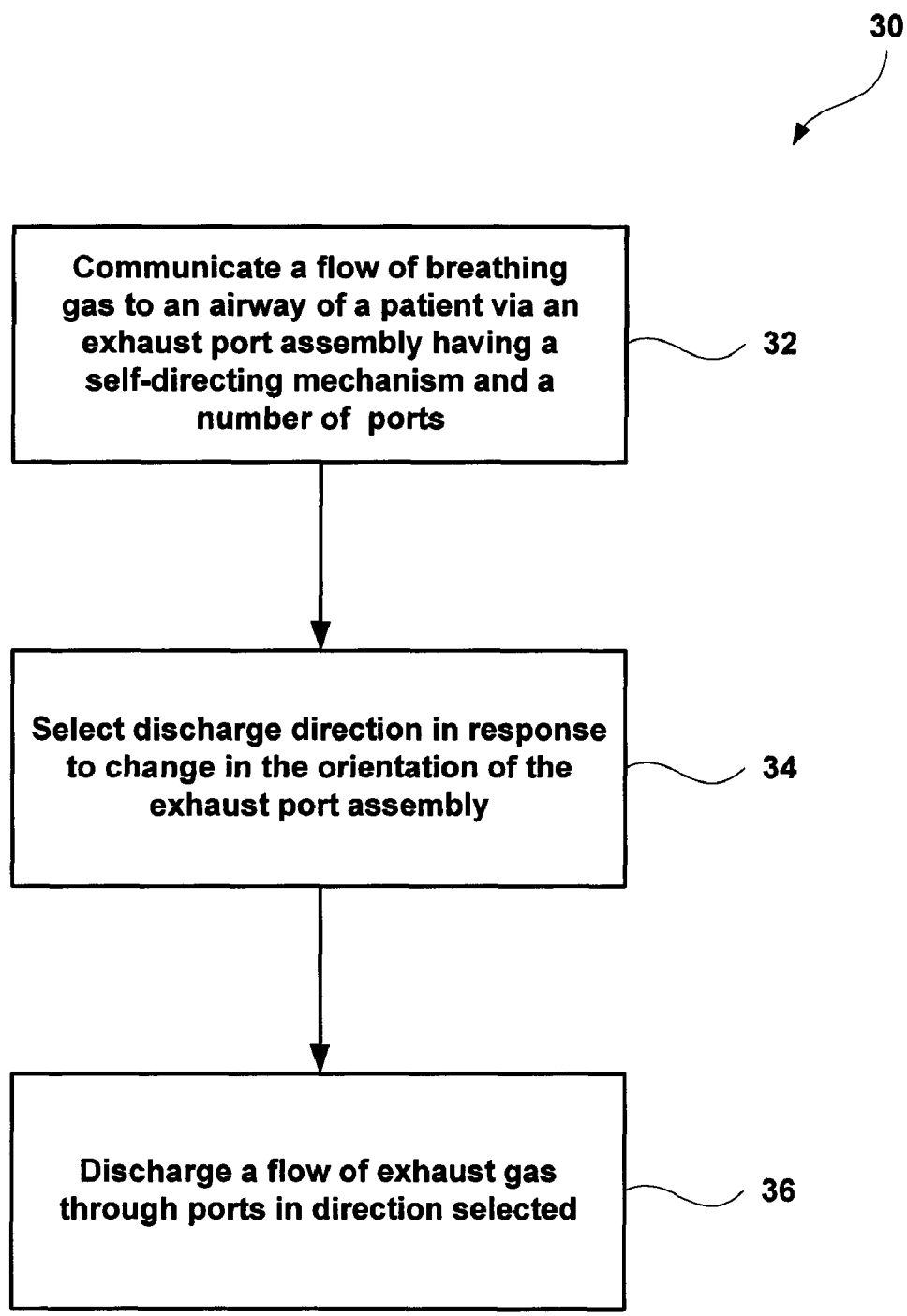
FIG. 10 is a diagram of an operational process for providing a breathing gas to a patient according to an embodiment of the present invention.

An operational process 30 for providing a breathing gas to a patient is illustrated in FIG. 10. Operational process 30 begins with operation 32 where a flow of breathing gas is communicated to an airway of such a patient via an exhaust port assembly having a self-directing mechanism and a number of exhaust ports. In the current embodiment, for example, the breathing gas is communicated via an exhaust port assembly 10 comprised of mechanism 18 with a number of ports 20 and a counter weight 22. As discussed above, exhaust port assembly 10 is adapted to freely rotate relative to axis 26. The flow of breathing gas is generated using pressure generating device 4 in the current embodiment.

Operational control is then passed to operation 34 where, in response to a change in the orientation of the exhaust port assembly, the direction of discharge of the flow of gas is automatically selected. In the current embodiment, in response to the change in orientation of the exhaust port assembly 10 (e.g., caused by a patient rolling onto his side), a motive force (here, gravitational force 25) acting upon counter weight 22 causes mechanism 18 to rotate about axis 26 (as indicated by arrow 27) such that the direction of discharge of the flow of gas is automatically selected (e.g., continues to point upward).

Operational control is then passed to operation 36 where a flow of exhaust gas is discharged through the ports in the selected direction. As discussed above, ports 20 and counter weight 22 are arranged such that the flow of exhaust gas is discharged through ports 20 and away from the airway of the patient. Although discussed in conjunction with exhaust port assembly 10, it is contemplated that any exhaust port assembly within the scope of the present invention may be utilized with operational process 30.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system adapted to provide a regimen of respiratory therapy to a patient, the system comprising:
   a gas flow generator structured to produce a flow of breathing gas;
   a patient interface device structured to communicate the flow of breathing gas to an airway of such a patient;
   an exhaust port assembly; and
   a patient circuit structured to couple the gas flow generator to the patient interface device,
   wherein the exhaust port assembly comprises a mechanism structured to control the direction of a flow of exhaust gas discharged from the patient interface device, wherein the mechanism includes a moveable member structured to move relative to a component of the patient interface device responsive to a motive force, the moveable member including an opening structured to permit the exhaust gas to flow through the moveable member, and a counter weight spaced from the opening on the moveable member, wherein the moveable member and the patient interface device are structured to permit the exhaust gas to flow through the opening regardless of a position of the moveable member relative to the component of the patient interface device.

2. The system of claim 1, wherein the component of the patient interface device includes a first set of exhaust ports structured to discharge the flow of exhaust gas in a first direction, and a second set of exhaust port structured to discharge the flow of exhaust gas in a second direction, and wherein the moveable member is structured to selectively permit the flow of exhaust gas through the opening and one of the first set of exhaust ports and the second set of exhaust ports depending on the position of the moveable member relative to the component of the patient interface device.

3. The system of claim 1, wherein the exhaust port assembly further comprises:
   an inlet member; and
   an outlet member,
   wherein the moveable member is moveably coupled to the inlet member and to the outlet member such that the component of the patient interface device is the inlet member and the outlet member, and wherein the moveable member is structured to remain substantially stationary relative to an axis through the inlet member and the outlet member when at least one of the inlet member and the outlet member rotate relative to the axis.

4. The system of claim 1, wherein the motive force is at least one of a gravitational force, an electro-magnetic force, and a magnetic force.

* * * * *